(12) United States Patent
Chewter et al.

(10) Patent No.: US 8,779,226 B2
(45) Date of Patent: *Jul. 15, 2014

(54) PROCESS FOR PREPARING ETHYLENE AND PROPYLENE

(75) Inventors: Leslie Andrew Chewter, Amsterdam (NL); Rajaram Ramesh, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,333

(22) Filed: Sep. 7, 2012

(65) Prior Publication Data
US 2013/0237715 A1 Sep. 12, 2013

(30) Foreign Application Priority Data
Sep. 7, 2011 (EP) .................................. 11180342

(51) Int. Cl.
*C07C 2/00* (2006.01)
(52) U.S. Cl.
USPC ............ 585/326; 549/523; 585/324; 585/640
(58) Field of Classification Search
USPC ........... 549/513, 523; 585/324, 326, 639, 640
See application file for complete search history.

(56) References Cited

U.S. PATENT DOCUMENTS

| | | | | |
|---|---|---|---|---|
| 6,049,017 A * | 4/2000 | Vora et al. | ...................... | 585/324 |
| 7,238,846 B2 * | 7/2007 | Janssen et al. | ................. | 585/640 |
| 7,247,764 B2 * | 7/2007 | Janssen et al. | ................. | 585/640 |
| 7,402,718 B2 * | 7/2008 | Janssen et al. | ................. | 585/638 |
| 7,932,427 B2 * | 4/2011 | Chewter et al. | ................. | 585/651 |
| 8,049,054 B2 * | 11/2011 | Chewter et al. | ................. | 585/643 |
| 8,269,056 B2 * | 9/2012 | Van Westrenen et al. | .... | 585/639 |
| 2005/0177009 A1 | 8/2005 | Levin et al. | | |
| 2007/0155999 A1 | 7/2007 | Pujado et al. | | |
| 2007/0203380 A1 | 8/2007 | Vora et al. | | |

FOREIGN PATENT DOCUMENTS

| | | |
|---|---|---|
| WO | 9321139 | 10/1993 |
| WO | 2004000765 | 12/2003 |
| WO | 2006020083 | 2/2006 |

OTHER PUBLICATIONS

Handbook of MTBE and Other Gasoline Oxygenates, H. Hamid and M.A. Ali ed., 1st edition, Marcel Dekker, New York, 2004, pp. 65 to 223.

* cited by examiner

*Primary Examiner* — Golam M M Shameem

(57) ABSTRACT

The present invention provides a process for preparing ethylene and/or propylene, comprising the steps of:
a) providing an oxygenate-comprising feedstock;
b) contacting the oxygenate-comprising feedstock with a molecular sieve-comprising catalyst at a temperature in the range of from 450 to 700° C. and converting at least part of the oxygenate into an olefinic product comprising ethylene and/or propylene; and
c) retrieving the olefinic product,
wherein the oxygenate-comprising feedstock comprises in the range of from 1 to 97 wt % of at least one tert-alkyl ether selected from the group MTBE, ETBE, TAME and TAEE, based on the weight of the oxygenates in the oxygenate-comprising feedstock, and further comprises methanol and/or DME.

14 Claims, No Drawings

PROCESS FOR PREPARING ETHYLENE AND PROPYLENE

This application claims the benefit of European Application No. 11180342.5 filed Sep. 7, 2011, which is incorporated herein by reference.

FIELD OF THE INVENTION

The invention relates to a process for preparing ethylene and/or propylene.

BACKGROUND TO THE INVENTION

Methanol-to-olefin processes are well described in the art. Typically, methanol-to-olefin processes are used to produce predominantly ethylene and propylene. An example of such a methanol-to-olefin process is described in WO-A 2006/020083. In the process of WO-A 2006/020083 the methanol is first converted into dimethylether (DME) prior to be subjected to a conversion to olefins, thereby reducing the amount of water produced during the conversion to olefins. Both methanol and DME are suitable feedstocks for a methanol-to-olefin process and therefore such processes are also generally referred to as oxygenate-to-olefin (OTO) processes.

In the process of WO-A 2006/020083, the methanol or DME is contacted with a catalyst at temperatures above 200° C. At temperatures above 200° C., and in particular above 350° C., however, an undesired decomposition of the methanol and/or DME can take please before the methanol and/or DME can be converted to the desired olefinic product. This decomposition may for instance take place during the preheating of the oxygenate feed or during the introduction of the oxygenate feed into the reactor by contact with metal surfaces of for instance the reactor wall, internals or nozzles. The metal in the metal surfaces catalyses the decomposition of methanol into hydrogen and carbon monoxide.

In for instance EP1513787 it is suggested to maintain the inner surface of the feed nozzles at a temperature below 350° C., even as low as 150° C., to prevent undesired decomposition of oxygenates in the feedstock leading to the formation of waste by-products.

However, this requires extensive cooling and insulation of the feed nozzles, while the feed is introduced into the reactor at a lower than desired temperature.

There is a need in the art for an OTO process wherein undesired decomposition of the feed is reduced.

SUMMARY OF THE INVENTION

It has now been found that the stability with respect to decomposition of the feed to waste by-products to an OTO process in contact with metal surfaces can be improved by using a feed that comprises one or more tert-alkyl ethers.

Accordingly, the present invention provides a process for preparing ethylene and/or propylene, comprising the steps of:
a) providing an oxygenate-comprising feedstock;
b) contacting the oxygenate-comprising feedstock with a molecular sieve-comprising catalyst at a temperature in the range of from 450 to 700° C. and converting at least part of the oxygenate into an olefinic product comprising ethylene and/or propylene; and
c) retrieving the olefinic product,
wherein the oxygenate-comprising feedstock comprises in the range of from 1 to 97 wt % of at least one tert-alkyl ether selected from the group MTBE, ETBE, TAME and TAEE, based on the weight of the oxygenates in the oxygenate-comprising feedstock, and further comprises methanol and/or DME.

Reference herein to a tert-alkyl ether is to an ether of an iso-olefin and an alkyl alcohol.

In contact with metals surfaces, the selected tert-alkyl ethers show reduced metal-induced waste by-product, including hydrogen and carbon monoxide, formation per mol of oxygenate during preheating and introduction into the reactor of the oxygenate-comprising feedstock, compared to methanol.

Furthermore, the selected tert-alkyl ethers may conveniently be combined with methanol to form the oxygenate-comprising feedstock. The selected tert-alkyl ethers have properties, such as density and boiling temperatures, comparable to methanol allowing the use of systems, designed for preheating and vaporisation of methanol-based oxygenate feedstocks, for tert-alkyl ethers comprising feedstocks with little or no adaptation.

Although, tert-alkyl ethers have boiling temperatures similar to that of for instance methanol and dimethylether, the heat of evaporation for tert-alkyl ethers is significantly lower compared to for instance methanol. For example, the heat of evaporation for MTBE is approximately 320 kJ/kg, whereas the heat of evaporation for methanol is approximately 1178 kJ/kg. Consequently, significantly less energy is required to vaporise the tert-alkyl ethers compared to methanol. By replacing at least part of a methanol feed to an existing OTO process by MTBE, more feedstock can be evaporated in the feed vaporiser for the same energy consumption, or the same amount of feedstock can be vaporised at a lower energy consumption.

Due to reduced demands for the selected tert-alkyl ethers as fuel components, a significant global production capacity of the selected tert-alkyl ethers is available, which can be used to provide oxygenate feedstock for the production of olefins such as ethylene and propylene.

The high ratio of carbon atoms to oxygen atoms in the tert-alkyl ethers allows for a high yield of olefins per mol of ether provided, at least higher than the yield obtained per mol of methanol or dimethylether.

DETAILED DESCRIPTION OF THE INVENTION

In the process according to the present invention, an oxygenate-comprising feedstock is provided in step (a). The oxygenate-comprising feedstock comprises at least one tert-alkyl ether selected from the group of Methyl Tert-Butyl Ether (MTBE), Ethyl Tert-Butyl Ether (ETBE), Tert-Amyl Methyl Ether (TAME) and Tert-Amyl Ethyl Ether (TAEE). These tert-alkyl ethers have a high stability to metal induced decomposition of the feed to waste by-products and are therefore less sensitive to the high temperatures to which they are exposed during preheating and vaporisation of the oxygenate-comprising feedstock and the temperatures of the feed introduction nozzles and inner walls of the OTO reactor.

The oxygenate-comprising feedstock may be a feedstock comprising oxygenates selected from the group consisting of MTBE, ETBE, TAME and TAEE. However, the oxygenate-comprising feedstock further comprises other oxygenates in particular methanol and/or DME and preferably methanol. The oxygenate-comprising feedstock comprises in the range of from 1 to 97 wt %, preferably 5 to 95 wt % of tert-alkyl ether, selected from the group of MTBE, ETBE, TAME and TAEE, based on the weight of the oxygenates in the oxygenate-comprising feedstock. By increasing the amount of tert-alkyl ether in the oxygenate-comprising feedstock, the effect of the stability to metal induced decomposition of the feed to waste by-products of the tert-alkyl ethers becomes more pronounced. In one preferred embodiment, the tert-alkyl ether, selected from the group of MTBE, ETBE, TAME and TAEE, is added to an oxygenate-comprising feedstock provided to a conventional OTO process. In that case, it is preferred that the tert-alkyl ether is added in an amount such that the oxygenate-comprising feedstock comprises in the range of from 0.01 to 50 wt % of tert-alkyl ether, based on the weight of the oxygenates in the oxygenate-comprising feedstock, more preferably in the range of from 0.5 to 20 wt % of tert-alkyl ether, even more preferably 1 to 10 wt % of tert-alkyl ether. Also preferably, the oxygenate-comprising feedstock comprises in the range of from 1 to 50 wt % of tert-alkyl ether, based on the weight of the oxygenates in the oxygenate-comprising feedstock, more preferably in the range of from 1 to 20 wt % of tert-alkyl ether, even more preferably 1 to 10 wt % of tert-alkyl ether. When the tert-alkyl ether is added to the oxygenate-comprising feedstock in such quantities, the existing OTO process may be operated with little or no need to modify the process conditions due to the addition of the tert-alkyl ether. This is particularly preferred in cases where insufficient oxygenate feedstock such as for instance methanol is available to utilize the full capacity of the OTO unit or in case the demand for ethylene and/or propylene temporarily or consistently exceeds the supply of methanol required to fulfil this demand. In another preferred embodiment, the oxygenate-comprising feedstock is provided to an OTO process comprising in the range of from 50 to 100 wt %, preferably of from 50 to 97 wt %, more preferably of from 60 to 95 wt %, of tert-alkyl ether, selected from the group of MTBE, ETBE, TAME and TAEE, based on the weight of the oxygenates in the oxygenate-comprising feedstock. This is particularly preferred when large volumes of tert-alkyl ethers are available at a production site, without an economically benign outlet for the tert-alkyl ethers. A further preferred embodiment, may comprise the initial use of an oxygenate feedstock comprising in the range of from 50 to 100 wt %, preferably of from 50 to 97 wt %, more preferably of from 60 to 95 wt %, of tert-alkyl ether, selected from the group of MTBE, ETBE, TAME and TAEE, based on the weight of the oxygenates in the oxygenate-comprising feedstock. Subsequently, the tert-alkyl ether concentration in the feed may be lowered, preferably lowered such that an oxygenate-comprising feedstock is used that comprises in the range of from 0.01 to 50 wt % of tert-alkyl ether, preferably of from 1 to 50 wt %, based on the weight of the oxygenates in the oxygenate-comprising feedstock, more preferably in the range of from 0.5 to 20 wt %, preferably of from 1 to 20 wt % of tert-alkyl ether, even more preferably 1 to 10 wt % of tert-alkyl ether. This embodiment is of particular use in case at the time of start-up insufficient methanol is available.

In step (b) of the process, the oxygenate-comprising feedstock is contacted with a molecular sieve-comprising catalyst at a temperature in the range of from 450 to 700° C. At these temperatures, at least part of the oxygenates in the oxygenate-comprising feedstock are converted into an olefinic product comprising ethylene and/or propylene, in the presence of the molecular sieve-comprising catalyst. The conversion of oxygenates such as methanol and DME, under such conditions, to olefins in the presence of molecular sieve-comprising catalysts is well known in the art. With respect to the tert-alkyl ethers it is believed, without wishing to be bound to a particular theory, that upon contacting the molecular sieve-catalyst, the tert-alkyl ether decomposes into its corresponding alcohol, i.e. methanol or ethanol, and iso-olefin, i.e. isobutene or isopentene. This decomposition reaction is acid-catalysed. Therefore, preferably the molecular sieve-comprising catalyst comprises acid groups. Some molecular sieves are acidic by nature, whereas other molecular sieve-comprising catalysts comprise binder, support, matrix or other materials comprising acid groups. Even theoretically non-acidic molecular sieves typically comprise some residual acid groups introduced during preparation of the molecular sieve and/or molecular sieve-comprising catalyst. In the absence of any acid groups in the molecular sieve-comprising catalyst it may be preferred to add such groups either by treating the molecular sieve-comprising catalyst to introduce such groups essentially at the surface of the catalyst through impregnation with an acid that resides on the catalyst after calcination, for instance by treating the molecular sieve-comprising catalyst with an acid, such as phosphoric acid, or adding an acid component to catalyst formulation comprising the molecular sieve-comprising catalyst, such as alumina.

Alternatively, the oxygenate-comprising feedstock is contacted with an acid catalyst, prior to contacting the molecular sieve-comprising catalyst. This may for instance be done by passing oxygenate-comprising feedstock through an acid catalyst comprising bed or by passing the feedstock through an acid grid or filter. Preferably, the oxygenate-comprising feedstock is contacted with the acid catalyst at a temperature above 150° C. More preferably, the oxygenate-comprising feedstock is contacted with the acid catalyst at a temperature above 350° C.

Preferably, steam is present as the tert-alkyl ether contacts the catalyst. Steam is believed to increase the rate of tert-alkyl ether decomposition reaction.

At least part of the methanol or ethanol obtained following the decomposition of the tert-alkyl ether is subsequently converted into an olefinic product comprising ethylene and/or propylene over the molecular sieve-comprising catalyst under the process conditions applied.

Preferably, the tert-alkyl ether is decomposed into at least methanol as methanol is one of the preferred oxygenate feedstocks for OTO processes, therefore it is preferred that the oxygenate-comprising feedstock comprises at least a tert-alkyl ether selected from the group of MTBE and TAME. Tert-alkyl ether selected from the group of MTBE and TAME are particularly preferred when the oxygenate-comprising feedstock further comprises methanol or DME. In that case, the operation conditions in the OTO process can be optimised for the conversion of methanol.

An advantage of having methanol or DME in the oxygenate feedstock next to the tert-alkyl ether is that the methanol or DMA may react with the iso-olefin to ethylene and propylene. By providing a molar excess of methanol or DME with respect to the iso-olefin provided to the process as part of the tert-alkyl ether may improve the conversion of the iso-olefin.

As mentioned hereinabove it is believed that upon contact with the molecular sieve-comprising catalyst, the tert-alkyl ether decomposes into its corresponding alcohol and an iso-olefin, i.e. isobutene or isopentene. Depending on the nature of the molecular sieve in the molecular sieve-comprising catalyst, the obtained iso-olefins are either, at least partially, converted to ethylene and/or propylene or remain unconverted and become part of olefinic product as such.

Preferably, the oxygenate-comprising feedstock is preheated to a temperature in the range of from 200 to 550° C., preferably 350 to 500° C. prior to contacting with the molecular sieve-comprising catalyst in step (b). By using an oxygenate-comprising feedstock that comprises at least one of the selected tert-alkyl ethers, by-product formation due to metal-induced decomposition of the oxygenates in the oxygenate-comprising feedstock may be reduced.

In step (c) of the process according to the present invention, the olefinic product is retrieved from the process. The olefinic product comprises ethylene and/or propylene, which may be separated from the remainder of the components in the olefinic product. Preferably, the olefinic product comprises advantageously at least 50 mol %, in particular at least 50 wt %, ethylene and propylene, based on total hydrocarbon content in the olefinic product. Where the olefinic product comprises ethylene, least part of the ethylene may be further converted into at least one of polyethylene, mono-ethyleneglycol, ethylbenzene and styrene monomer. Where the olefinic product comprises propylene, at least part of the propylene may be further converted into at least one of polypropylene and propylene oxide.

Other components in the olefinic product may include, but are not limited to, methane, C4+ hydrocarbons, including olefins and paraffins, and water. The C4+ hydrocarbons in the olefinic product are herein also referred to as the C4+ hydrocarbon fraction. This C4+ hydrocarbon fraction comprises at least C4+ olefins. The C4+ olefins in the C4+ hydrocarbon fraction may originate from the decomposition of the tertalkyl ethers. Generally, these olefins will be iso-olefins, in particular isobutene and isopentene, depending on the tertalkyl ether in the oxygenate-comprising feedstock. Preferably, the molar ratio of iso-olefins to normal-olefins in the C4+ hydrocarbon fraction is higher than the molar ratio of iso-olefins to normal-olefins in a C4+ hydrocarbon fraction obtained when an oxygenate-comprising feedstock comprising an oxygenate selected from the group consisting of consisting of methanol and dimethylether is used. The C4+ olefins in the C4+ hydrocarbon fraction may also be formed as part of the OTO process or be unconverted olefins introduced as part of the oxygenate-comprising feedstock. The C4+ hydrocarbon fraction may be, at least in part, separated from the remainder of the olefinic product and at least partially recycled to the OTO process in step (b) as an olefinic co-feed as part of or together with the oxygenate-comprising feedstock. This is particularly preferred if the molecular sievecomprising catalyst in step (b) facilitates the conversion of olefins to ethylene and/or propylene. Catalysts suitable for converting olefins to ethylene and/or propylene include for instance zeolite-comprising catalysts.

Alternatively, but equally preferred, the C4+ hydrocarbon fraction is at least partially converted by contacting, at least part of, the C4+ hydrocarbon fraction in a separate unit with a zeolite-comprising catalyst in a further step (d). This is particularly preferred where molecular sieve-comprising catalyst in step (b) comprises at least one SAPO, AlPO, or MeAlPO type molecular sieve, preferably SAPO-34. These catalysts are less suitable for converting iso-olefins. Preferably, the C4+ hydrocarbon fraction is contacted with the zeolite-comprising catalyst at a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar). Optionally, the stream comprising C4+ olefins also contains a diluent. Examples of suitable diluents include, but are not limited to, water or steam, nitrogen, argon and methane. Under these conditions, at least part of the olefins in the C4+ hydrocarbon fraction are converted to a further olefinic product comprising ethylene and/or propylene. The further olefinic product may be combined with the olefinic product obtained in step (b). Such a separate process step directed at converting C4+ olefins to ethylene and propylene is also referred to as an olefin cracking process (OCP).

In the present invention, an oxygenate-comprising feedstock is converted in an oxygenate-to-olefins process, in which an oxygenate feedstock is contacted in an OTO zone with an oxygenate conversion catalyst under oxygenate conversion conditions, to obtain a conversion effluent comprising lower olefins. Reference herein to an oxygenate feedstock is to an oxygenate-comprising feedstock. In the OTO zone, at least part of the feedstock is converted into an olefinic product, i.e. a product containing one or more olefins, including ethylene and/or propylene.

The oxygenate-comprising feedstock comprises at least one tert-alkyl ether selected from the group of MTBE Methyl Tert-Butyl Ether (MTBE), Ethyl Tert-Butyl Ether (ETBE), Tert-Amyl Methyl Ether (TAME) and Tert-Amyl Ethyl Ether (TAEE). Other tert-alkyl ethers may be comprised in the feedstock, such as tert-alkyl ethers obtained by the reaction between a C3+ alkyl alcohol and a C6+ iso-olefin. However, these are less preferred, due to the more unpredictable conversion of the corresponding C3+ alkyl alcohol and a C6+ iso-olefin in the OTO reaction. The MTBE, ETBE, TAME and TAEE alkyl ethers may be produced by any suitable process for producing MTBE, ETBE, TAME and TAEE alkyl ethers available. Reference is made to the Handbook of MTBE and Other Gasoline Oxygenates, H. Hamid and M. A. Ali ed., 1$^{st}$ edition, Marcel Dekker, New York, 2004, pages 65 to 223, where several established process and catalyst for preparing MTBE, ETBE, TAME and TAEE alkyl ethers are described. In particular reference is made to chapter 9, pages 203 to 220 of the Handbook of MTBE and Other Gasoline Oxygenates, wherein suitable commercial etherification processes are described. The MTBE, ETBE, TAME and TAEE alkyl ethers may for instance be obtained from existing MTBE, ETBE, TAME and TAEE production facilities. Due to increasing restriction on the use of MTBE, ETBE, TAME and TAEE as fuel additives, significant capacity for producing MTBE, ETBE, TAME and TAEE as a feedstock to the process according to the present invention is available. It is an advantage of the present invention that the MTBE, ETBE, TAME and TAEE tert-alkyl ethers may conveniently be transported in bulk by truck or ship from a MTBE, ETBE, TAME and TAEE production site to the site where the process according to the present invention is operated. The MTBE, ETBE, TAME and TAEE may be provided, transported and/ or stored as an essentially pure compound or combined with methanol or ethanol. Due to the nature of the production process of the tert-alkyl ether, methanol or ethanol may be present in the crude tert-alkyl ether product obtained from a tert-alkyl ether production process. In addition, the crude tert-alkyl ether product may comprise some C4 and/or C5 olefins. In the process according to the invention, there is no need to separate such methanol and/or ethanol from the tertalkyl ether. Moreover, the crude tert-alkyl ether product may be used as such as part of the oxygenate-comprising feedstock.

The oxygenates used in the process according to the invention include at least one tert-alkyl ether selected from the group of MTBE, ETBE, TAME and TAEE. Further oxygenates that may be present and preferably are oxygenates, which comprise at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenatecomprising feedstock include alcohols and ethers. Examples of preferred oxygenates include alcohols, such as methanol, ethanol, propanol; and dialkyl ethers, such as dimethylether, diethylether, methylethyether. Preferably, the further oxygenate is methanol or dimethylether, or a mixture thereof.

Preferably the oxygenate-comprising feedstock comprises at least 50 wt % of oxygenate, based on the total of hydrocarbons and oxygenates in the oxygenate-comprising feedstock, more preferably at least 70 wt %.

The oxygenate feedstock can comprise an amount of diluents. During the conversion of the oxygenates, steam is produced as a by-product, which serves as an in-situ produced diluent. Optionally additional steam is added as diluent. The amount of additional diluent that needs to be added depends on the in-situ water make, which in turn depends on the composition of the oxygenate-comprising feed. Where methanol produces 1 mol of water per mol of carbon atoms supplied to the process, MTBE, for example only produces 0.20 mol of water per 1 mol of carbon atoms supplied to the process. Where the diluent is water or steam, the molar ratio of oxygenate to diluent is between 10:1 and 1:20. In case, the oxygenate-comprising feedstock comprises in the range of from 0.01 to 50 wt %, preferably of from 1 to 10 wt %, of tert-alkyl ether, based on the oxygenates in the oxygenate-comprising feedstock, the molar ratio of oxygenate to diluent is preferably in the range of from 3:1 to 1:5, preferably 2:1 to 1:2. In case, the oxygenate-comprising feedstock comprises in the range of from 50 to 100 wt %, preferably 60 to 95 wt %, of tert-alkyl ether, based on the oxygenates in the oxygenate-comprising feedstock, the molar ratio of oxygenate to diluent is preferably in the range of from 1:3 to 1:15, preferably 1:4 to 1:10.

Due to the low in-situ water make of tert-alkyl ethers, the use of diluents other than water may be preferred, in particular when the catalyst is sensitive to hydrothermal deactivation. Other suitable diluents include inert gases such as nitrogen o methane, but may also include C2-C3 paraffins.

Preferably, in addition to the oxygenate, an olefinic co-feed is provided along with and/or as part of the oxygenate feedstock. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species.

Preferably, at least 70 wt % of the olefinic co-feed, during normal operation, is formed by a recycle stream of a C4+ hydrocarbon fraction from the OTO conversion effluent, preferably at least 90 wt % of olefinic co-feed, based on the whole olefinic co-feed, is formed by such recycle stream. In order to maximize production of ethylene and propylene, it is desirable to maximize the recycle of C4 olefins in the effluent of the OTO process. As described herein above, this can be done by recycling at least part of the C4+ hydrocarbon fraction, preferably a C4-C5 hydrocarbon fraction, more preferably C4 hydrocarbon fraction, in the olefinic product, which is retrieved as the OTO effluent. However, a certain part thereof, such as between 1 and 5 wt %, needs to be withdrawn as purge, since otherwise saturated hydrocarbons, in particular C4 saturated hydrocarbons (butane) would build up in the process, which are substantially not converted under the OTO reaction conditions.

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably the molar ratio of oxygenate to olefin in the total feed, oxygenate-comprising feedstock and olefinic co-feed, lies in the range of 20:1 to 1:10, more preferably in the range of 18:1 to 1:5, still more preferably in the range of 15:1 to 1:3, even still more preferably in the range of 12:1 to 1:3. For purposes of calculating the molar ratio of oxygenate to olefin in the total feed, the olefins provided to the process as part of the tert-alkyl ether must also be taken into account.

A further advantage of using the selected tert-alkyl ethers as part of the oxygenate-comprising feedstock is that these ethers provide both an oxygenate, being methanol or ethanol, and an olefin, being isobutene or isopentene, to the process in the form of a single molecule, which decomposes when contacted with the catalyst. This has the advantage that both reactants, i.e. an oxygenate and an olefin, may be provided in a single feed component. This allows for instance a more convenient transport of the feedstock, storage of the feedstock and pretreatment of the feedstock. In addition, where C4 olefins are gaseous under ambient conditions, the selected tert-alkyl ethers are liquids under ambient conditions having a significantly higher density than the gaseous C4 olefins. Furthermore, the handling and storage of liquids is less complicated, providing further advantages.

A variety of OTO processes is known for converting oxygenates to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for converting the oxygenate-comprising feedstock preferably include molecular sieve-comprising catalyst compositions. Such molecular sieve-comprising catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Aluminosilicate-comprising catalysts, and in particular zeolite-comprising catalysts, have the additional advantage that in addition to the conversion of methanol or ethanol, these catalysts also induce the conversion of olefins to ethylene and/or propylene. As a result, at least part of the olefins obtained as the tert-alkyl ether is decomposed into methanol or ethanol and the corresponding iso-olefin, may also be converted into ethylene and/or propylene. Furthermore, these aluminosilicate-comprising catalysts, and in particular zeolite-comprising catalysts, are particularly suitable for use as the catalyst in an OCP. Particular preferred catalyst for the OCP reaction, i.e. converting part of the olefinic product, and preferably part of the C4+ hydrocarbon fraction of the olefinic product including olefins, are catalysts comprising at least one zeolite selected from MFI, MEL, TON and MTT type zeolites, more preferably at least one of ZSM-5, ZSM-11, ZSM-22 and ZSM-23 zeolites.

In one preferred embodiment, the molecular sieve in the molecular sieve-comprising catalyst of step (b) is a non-zeolitic molecular sieve, while part of the olefinic product retrieved in step (c), in particular at least part of the C4+ fraction containing olefins, is provided to a subsequent separate OCP unit with a zeolite-comprising catalyst and the C4+ hydrocarbon fraction is at least partially converted by contact with the zeolite-comprising catalyst.

Preferred catalysts, for both the OTO reaction in step (b) as well as an optional OCP reaction in step (d), comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80. The oxygenate conversion catalyst can comprise at least 1 wt %, based on total molecular sieve in the oxygenate conversion catalyst, of the second molecular sieve having more-dimensional channels, preferably at least 5 wt %, more preferably at least 8 wt %.

Particular preferred catalysts include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites based on total zeolites in the catalyst.

In a particularly preferred embodiment the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may comprise phosphorous as such or in a compound, i.e. phosphorous other than any phosphorous included in the framework of the molecular sieve. It is preferred that a MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorous as such or in a compound in an elemental amount of from 0.05 to 10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

It is preferred that the molecular sieves in the hydrogen form are used in the oxygenate conversion catalyst, e.g., HZSM-22, HZSM-23, and HZSM-48, HZSM-5. Preferably at least 50 wt %, more preferably at least 90 wt %, still more preferably at least 95 wt % and most preferably 100 wt % of the total amount of molecular sieve used is in the hydrogen form. It is well known in the art how to produce such molecular sieves in the hydrogen form.

The reaction conditions of the oxygenate conversion in step (b) include a reaction temperature of 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve. This applies to both the catalyst used in step (b) of the process as well as the catalyst in the optional step (d) of the process.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 μm, preferably 50-100 μm.

Both the OTO process of step (b) as the optional OCP process of step (d) may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

EXAMPLES

The invention is illustrated by the following non-limiting examples.

Example 1a

The thermal stability of MTBE was tested. To test the thermal stability, the MTBE was fed to a quartz reactor tube of 1.8 mm internal diameter. A mixture consisting of 6 vol % MTBE, balanced in $N_2$ was passed through the quartz reactor tube at atmospheric pressure (1 bar). The total gas flow rate was 9.1 ml/min. The effluent from the reactor was analyzed by gas chromatography (GC) to determine the product composition. The composition has been calculated on a weight basis of all hydrocarbons analyzed. The effluent from the reactor obtained at several reactor temperatures was analyzed. The results are shown in Table 1a.

It is clear from table 1a, that MTBE remains intact at temperatures as high as 310° C. Above 525° C., some decomposition of MTBE into methanol and isobutene (iC4=) is observed. However, no formation of hydrogen and carbon monoxide is observed. It can be concluded that no subsequent decomposition of methanol to hydrogen and carbon monoxide is observed. No formation of dimethylether (DME) is observed.

TABLE 1a

| T [° C.] | MTBE [wt %] | MeOH [wt %] | DME [wt %] | iC4= [wt %] |
|---|---|---|---|---|
| 150 | 99.6 | 0.1 | 0.0 | 0.3 |
| 310 | 98.8 | 0.4 | 0.0 | 0.9 |
| 525 | 82.1 | 6.3 | 0.0 | 11.6 |

Example 1b

The thermal stability of MTBE was tested in the presence of a metal surface. To test the thermal stability in the presence of a metal surface, the MTBE was fed to a quartz reactor tube of 1.8 mm internal diameter comprising a non-woven stainless steel mesh. A mixture consisting of 6 vol % MTBE, balanced in $N_2$ was passed through the quartz reactor tube at atmospheric pressure (1 bar) and heated with ramp rate of 2.5 C/min starting at 100 C to 600 C. The Gas Hourly Space Velocity (GHSV) is determined by the total gas flow over the stainless steel mesh weight per unit time (ml·g stainless steel mesh$^{-1}$·h$^{-1}$). The gas hourly space velocity used was 7000 (ml·g stainless steel mesh$^{-1}$·h$^{-1}$). The effluent from the reactor was analyzed by Mass Spectrometry (MS) to determine the product composition. The composition has been calculated on basis of all hydrocarbons analyzed. The effluent from the reactor obtained at several reactor temperatures was analyzed.

Comparative Example A

Following the same procedure as for Example 1B, the thermal stability of methanol was determined by feeding a mixture consisting of 6 vol % methanol, balanced in $N_2$ through quartz reactor tube at atmospheric pressure (1 bar).

During the experiment of comparative Example A, it was observed that the methanol concentration in the effluent rapidly decreased as the temperature was increased above 325° C., indicating methanol decomposition. However, in the experiment of Example 1b, it was found that methanol concentrations in the effluent increased with increasing temperature. The emergence of methanol in the effluent of the experiment of Example 1b, where the feed consisted of a mixture of MTBE and nitrogen is caused by the fact that part of the MTBE decomposes to methanol and isobutene at temperatures above 200° C. As the temperature was further increased more MTBE was decomposed. To determine if the methanol, obtained by the decomposition, is subsequently also decomposed, the hydrogen concentration in the effluent was measured. Hydrogen is one of the decomposition products of methanol. As can be seen from table 1b, the hydrogen content in the effluent in case methanol is used as a feedstock increased rapidly above 325° C., indicating methanol decomposition in the presence of the stainless steel mesh. However, in case of a MTBE feed, little hydrogen is found in the effluent indicating that little methanol decomposition takes place in the presence of the stainless steel mesh.

TABLE 1b

| T [° C.] | Example 1b MTBE feed $H_2$ in effluent [mol %] | Comparative Example A MeOH feed $H_2$ in effluent [mol %] |
|---|---|---|
| 200 | 0 | 0 |
| 300 | 0 | 0 |
| 325 | 0.1 | 0 |
| 350 | 0.2 | 0.03 |
| 375 | 0.3 | 0.3 |
| 400 | 0.4 | 1.1 |
| 425 | 0.4 | 2.4 |
| 450 | 0.5 | 3.6 |
| 475 | 0.7 | 5.0 |
| 500 | 1.2 | 7.8 |
| 525 | 1.6 | 12.4 |

Example 2

Several molecular sieves were tested to show their ability to convert MTBE to an olefinic product. To test the molecular sieves for catalytic performance, a powder of the respective molecular sieves was pressed into tablets and the tablets were broken into pieces and sieved. MTBE was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the reaction temperature and a mixture consisting of 6 vol % MTBE balanced in $N_2$ was passed over the catalyst at atmospheric pressure (1 bar). The Gas Hourly Space Velocity (GHSV) is determined by the total gas flow over the zeolite weight per unit time (ml·gzeolite$^{-1}$·h$^{-1}$). The gas hourly space velocity used in the experiments was 10000 (ml·gzeolite$^{-1}$·h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The effluent from the reactor obtained at several reactor temperatures was analyzed. The results are shown in Table 2.

TABLE 2

| T [° C.] | Catalyst | C2= [wt %] | C3= [wt %] | C4= [wt %] | C5= [wt %] | C1 [wt %] | C6+ [wt %] | C4 paraffin [wt %] |
|---|---|---|---|---|---|---|---|---|
| 420 | SAPO-34 | 7.90 | 15.15 | 65.43 | 9.18 | 0.19 | 1.06 | 1.09 |
| 525 | SAPO-34 | 9.41 | 18.17 | 50.01 | 14.78 | 1.57 | 2.58 | 3.49 |
| 420 | ZSM-5* | 10.86 | 28.10 | 15.93 | 8.13 | 0.12 | 23.56 | 13.31 |
| 525 | ZSM-5* | 26.77 | 38.11 | 11.46 | 2.69 | 0.03 | 13.01 | 7.92 |
| 525 | ZSM-5# | 17.89 | 39.85 | 25.49 | 3.22 | 1.79 | 9.69 | 2.07 |

TABLE 2-continued

| T [° C.] | Catalyst | C2= [wt %] | C3= [wt %] | C4= [wt %] | C5= [wt %] | C1 [wt %] | C6+ [wt %] | C4 paraffin [wt %] |
|---|---|---|---|---|---|---|---|---|
| 525 | ZSM-23 | 20.73 | 42.89 | 29.00 | 2.05 | 0.59 | 3.62 | 1.12 |
| 525 | ZSM-22 | 17.19 | 39.88 | 35.52 | 2.12 | 0.44 | 3.99 | 0.86 |

*SAR 80
SAR 280

For all tested catalyst, the conversion of MTBE was complete. No MTBE or methanol was detected in the effluent of the reactor.

The zeolite catalysts, i.e. ZSM-5, ZSM-22 and ZSM-23, show a good conversion of the MTBE, including the isobutene part of the MTBE, to ethylene and propylene. An advantage of the one-dimensional zeolites having 10-membered ring channels, i.e. ZSM-22 and ZSM-23, is the lower paraffin make and C6+ make compared to the multi-dimensional ZSMS zeolites.

By reducing the SAR of the ZSM-5 catalyst, the ethylene and propylene yield is improved, while significantly less C4 olefins are produced.

The non-zeolite SAPO-34 catalyst shows a low paraffin make and C6+ make, however is less suitable for converting C4 olefins as can be seen from the relative high C4 olefin content in the effluent of the reactor. These C4 olefins are preferably subsequently converted in an OCP reactor over a zeolite catalyst. It will be clear from table 2, that zeolite catalyst show a better conversion of C4 olefins to the desired ethylene and propylene products. Increasing the reaction temperature, results in a reduction of the C4 olefin content in the effluent of the reaction.

Example 3

Several molecular sieves were tested to show their ability to convert MTBE to an olefinic product. To test the molecular sieves for catalytic performance, a powder of the respective molecular sieves was pressed into tablets and the tablets were broken into pieces and sieved. MTBE was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to 525° C. and a mixture consisting of 3 vol % MTBE and 3 vol % methanol, balanced in $N_2$ was passed over the catalyst at atmospheric pressure (1 bar). The Gas Hourly Space Velocity (GHSV) is determined by the total gas flow over the zeolite weight per unit time (ml·gzeolite$^{-1}$·h$^{-1}$).

The gas hourly space velocity used in the experiments was 10000 (ml·gzeolite$^{-1}$·h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The results are shown in Table 3.

TABLE 3

| T [° C.] | Catalyst | C2= [wt %] | C3= [wt %] | C4= [wt %] | C5= [wt %] | C1 [wt %] | C6+ [wt %] | C4 paraffin [wt %] |
|---|---|---|---|---|---|---|---|---|
| 525 | SAPO-34 | 18.11 | 22.08 | 44.94 | 8.23 | 2.94 | 1.64 | 2.05 |
| 525 | ZSM-5* | 25.72 | 37.64 | 11.57 | 3.24 | 0.65 | 13.79 | 7.41 |
| 525 | ZSM-5# | 17.66 | 42.42 | 20.31 | 3.31 | 1.82 | 12.88 | 1.61 |
| 525 | ZSM-23 | 21.45 | 46.66 | 21.09 | 2.77 | 0.81 | 6.16 | 1.06 |
| 525 | ZSM-22 | 17.84 | 48.46 | 24.30 | 2.61 | 0.83 | 5.24 | 0.71 |

*SAR 80
SAR 280

Contrary to the non-zeolite SAPO-34 catalyst, the zeolite catalysts do not show a significant change in the obtained C2 to C4 olefinic product slate, when methanol is added to the MTBE feed. As a result, it can be expected that for an existing methanol based OTO process using a zeolite catalyst, MTBE can be blended into the methanol feed without requiring significant changes to the process operation.

What is claimed is:

1. A process for preparing ethylene and/or propylene, comprising the steps of:
    a) providing an oxygenate-comprising feedstock;
    b) contacting the oxygenate-comprising feedstock with a molecular sieve-comprising catalyst at a temperature in the range of from 450 to 700° C. and converting at least part of the oxygenate into an olefinic product comprising ethylene and/or propylene; and
    c) retrieving the olefinic product,
    wherein the oxygenate-comprising feedstock comprises in the range of from 1 to 97 wt % of at least one tert-alkyl ether selected from the group MTBE, ETBE, TAME and TAEE, based on the weight of the oxygenates in the oxygenate-comprising feedstock, and further comprises methanol and/or DME.

2. A process according to claim 1, wherein the oxygenate-comprising feedstock comprises at least one tert-alkyl ether selected from the group MTBE and TAME.

3. A process according to claim 1, wherein the oxygenate-comprising feedstock further comprises methanol.

4. A process according to claim 1, wherein the oxygenate-comprising feedstock comprises in the range of from 1 to 10 wt % of tert-alkyl ether, based on the oxygenates in the oxygenate-comprising feedstock.

5. A process according to claim 1, wherein the oxygenate-comprising feedstock comprises in the range of from 60 to 95 wt % of tert-alkyl ether, based on the oxygenates in the oxygenate-comprising feedstock.

6. A process according to claim 1, wherein the oxygenate-comprising feedstock further comprises C4+ olefins.

7. A process according to claim 1, further comprising recycling at least part of the olefinic product, preferably at least part of a C4+ hydrocarbon fraction of the olefinic product, back to step (b) as part of or together with the oxygenate-comprising feedstock.

8. A process according to claim 1, comprising a further step:
   d) contacting at least part of the olefinic product, preferably at least part of a C4+ hydrocarbon fraction of the olefinic product, with a zeolite-comprising catalyst at a temperature in the range of from 350 to 1000° C. and converting at least part of the olefinic product into a further olefinic product comprising ethylene and/or propylene.

9. A process according to claim 8, wherein the zeolite-comprising catalyst comprises at least one zeolite selected from MFI, MEL, TON and MTT type zeolites.

10. A process according to claim 8, wherein the molecular sieve-comprising catalyst comprises at least one SAPO, AlPO, or MeAlPO type molecular sieve.

11. A process according to claim 9, wherein the molecular sieve-comprising catalyst comprises at least one SAPO, AlPO, or MeAlPO type molecular sieve.

12. A process according to claim 1, wherein the oxygenate-comprising feedstock is preheated to a temperature in the range of from 200 to 550° C. prior to contacting with the molecular sieve-comprising catalyst in step (b).

13. A process according to claim 1, wherein the olefinic product comprises ethylene and at least part of the ethylene is further converted into at least one of polyethylene, mono-ethylene-glycol, ethylbenzene and styrene monomer.

14. A process according to claim 1, wherein the olefinic product comprises propylene and at least part of the propylene is further converted into at least one of polypropylene and propylene oxide.

* * * * *